(12) United States Patent
Boisjolie et al.

(10) Patent No.: US 12,080,430 B1
(45) Date of Patent: Sep. 3, 2024

(54) CARE PLAN MANAGEMENT

(71) Applicant: Baystate Health, Inc., Springfield, MA (US)

(72) Inventors: Nicholas Boisjolie, Southampton, MA (US); Kenneth Riley, Belchertown, MA (US)

(73) Assignee: Baystate Health, Inc., Springfield, MA (US)

( * ) Notice: Subject to any disclaimer, the term of this patent is extended or adjusted under 35 U.S.C. 154(b) by 329 days.

(21) Appl. No.: 17/547,579

(22) Filed: Dec. 10, 2021

Related U.S. Application Data

(60) Provisional application No. 63/123,857, filed on Dec. 10, 2020.

(51) Int. Cl.
*G16H 50/20* (2018.01)

(52) U.S. Cl.
CPC .................................. *G16H 50/20* (2018.01)

(58) Field of Classification Search
CPC ..................................................... G16H 50/20
See application file for complete search history.

(56) References Cited

U.S. PATENT DOCUMENTS

| | | | |
|---|---|---|---|
| 8,015,034 B2 | 9/2011 | Zhou et al. | |
| 8,700,431 B2 | 4/2014 | Ryan et al. | |
| 9,449,355 B2 | 9/2016 | Kozicki et al. | |
| 10,095,841 B2 | 10/2018 | Dettinger et al. | |
| 10,311,211 B2 | 6/2019 | Dettinger et al. | |
| 10,402,928 B2 | 9/2019 | Haque et al. | |
| 10,467,383 B2 | 11/2019 | Dettinger et al. | |
| 10,504,198 B1 | 12/2019 | Ward | |
| 10,510,444 B2 | 12/2019 | Dettinger et al. | |
| 10,529,446 B2 * | 1/2020 | Boland | G16H 40/67 |
| 10,636,517 B1 | 4/2020 | Teague et al. | |
| 11,094,405 B2 | 8/2021 | Brady | |
| 2010/0017228 A1 | 1/2010 | Ryan et al. | |
| 2012/0221352 A1 | 8/2012 | Georgeff | |
| 2015/0363569 A1 | 12/2015 | Ryan et al. | |

(Continued)

FOREIGN PATENT DOCUMENTS

EP 3599616 A1 * 1/2020 ............. G06N 3/045

OTHER PUBLICATIONS

Lapane, Kate L; Hiris, Jeffrey; Hughes, Carmel M; Feinberg, Janice. "Development and implementation of pharmaceutical care planning software for nursing homes based on the Fleetwood Model." American Journal of Health-System Pharmacy 63.24: 2483(5). American Society of Health-System Pharmacists. (Year: 2006).*

*Primary Examiner* — Linh Giang Le
(74) *Attorney, Agent, or Firm* — Bulkley, Richardson, and Gelinas, LLP

(57) ABSTRACT

A system and method for preparing, modifying, and administering a coordinated health care plan for a person receiving services from multiple providers that allow various user controlled devices speaking different machine and database languages to communicate with and contribute to a central database and processing unit that can interpret the variously expressed data, understand their relationships, establish linkages and consequences among the data, adjust a unified care management plan accordingly, and selectively communicate those consequences to appropriate provider, payor, and patient nodes in their respective machine and database languages.

18 Claims, 6 Drawing Sheets

(56) References Cited

U.S. PATENT DOCUMENTS

| | | |
|---|---|---|
| 2018/0157799 A1 | 6/2018 | Ketterer et al. |
| 2019/0006033 A1 | 1/2019 | Wolthuis et al. |
| 2019/0139633 A1 | 5/2019 | Zhu et al. |
| 2020/0013507 A1 | 1/2020 | Braun et al. |
| 2020/0111550 A1 | 4/2020 | Boland et al. |
| 2020/0118673 A1 | 4/2020 | Dettinger et al. |
| 2020/0273564 A1 | 8/2020 | Dettinger et al. |
| 2021/0358627 A1 | 11/2021 | Longmire et al. |

\* cited by examiner

CARE PLAN MANAGEMENT

RELATED APPLICATIONS

This application claims priority to U.S. Provisional Patent Application No. 63/123,857, filed Dec. 10, 2020, which is incorporated herein by reference in its entirety.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND OF THE INVENTION

Since at least the reemergence of the Health Maintenance Organization as a healthcare services model in the 1970s, efforts have been made to develop methods and systems that improve coordination among multiple healthcare providers contributing to the care of an individual.

A relatively recent movement to develop a better cooperative care system is the Accountable Care Organization (ACO). ACOs in the United States are formed from a group of coordinated health-care practitioners and are "accountable" to patients for the quality, cost, appropriateness, and efficiency of the services its associated professionals provide across the continuum of care. An ACO may include various medical professionals, related providers, and payors, such as doctors of medicine, doctors of osteopathic medicine, physician assistants, nurse practitioners, and clinical nurse specialists in group practice arrangements, networks of individual practices, partnerships or joint venture arrangements between hospitals and ACO professionals, hospitals employing ACO professionals, health departments, social security departments, insurers, safety net clinics, and home care services. Patients may participate in their ACO's decision-making processes. The ACO's goal is to incentivize these players to form linkages and facilitate coordination of care delivery to the patients.

The challenges faced by these efforts are both amplified and, in part, addressed by the increasing reliance upon digitization of health records and other medical information. If designed purposefully and implemented in a cost-effective way, digital solutions can support the continuity and coordination of care among diverse providers, which can support the reform of health systems and their transition from hospital-centered systems to more community-based, integrated care structures. They also have the potential to enable a better use of health data to support personalized healthcare, better health interventions, and more effective health and social care systems.

At the heart of digitalized health data is the electronic health record (EHR). An EHR is a digital version of a patient's paper chart that makes information potentially available instantly and securely to authorized users. EHRs allow providers to automate and streamline workflow and to access computer-based tools to aid decision making about a patient's care. Among other information, EHRs may contain a patient's medical history, diagnoses, medications, treatment plans, immunization dates, allergies, radiology images, and laboratory and test results. One of the key features of EHRs is that they have the potential to quickly share health information among providers and payors across multiple health care organizations involved in a patient's care such as laboratories, specialists, medical imaging facilities, community health workers, pharmacies, emergency facilities, insurance companies, and school and workplace clinics.

Health data within EHRs, however, is confidential, generally sensitive information that may be expressed in different formats and transmitted in different machine and database languages. The data also are managed in different ways by different providers, even within the same geographic region and sometimes even within the same organization. Furthermore, each care or services provider typically develops their own care plan for a patient. Methods for sharing of care plans for a patient, and modifications thereof, among the patient's providers are currently inconsistent and inefficient. Where the storage, analysis, and communication of health data and associated care plans depend on technologies that are not interoperable, the use of those data and plans, and the ability of medical providers to continually monitor a patient's medical records for updated information, are substantially hindered, making some of the data essentially unavailable to some providers and public authorities, and perhaps the patients themselves. These inefficiencies increase risk of improper or redundant tests or treatment that may not be in the best interests of the patient, cost effective, or eligible for provider reimbursement. The complexities involved in handling these data are compounded by their confidential nature and associated regulatory requirements.

Care management software intended to address some of these issues has been developed by others. For example, Ryan, et al. (US 2015/0363569) discloses a generalized method and system directed to providing a personalized patient care plan that is customizable based on a healthcare role associated with a user and that is shared among healthcare providers associated with multiple venues. Ryan includes the concept of sharing the customized plans among providers and using data provided by all providers to inform the creation and modification of each individualized plan. The process presented, however, is non-specific, describing a generalized concept of extracting, from a patient's overall set of healthcare data, a set of data that is relevant for a particular healthcare provider and populating those data as a set of care items in a care plan for the patient that is personalized for that provider.

These systems, however, do not address the needs of providers, payors, and patients operating through comprehensive care organizations, such as an ACO, with diverse providers utilizing diverse EHRs that support their individual specialty and practices workflow where specialty and practice specific care plans are developed for an individual without the more complete care plan context from every individual included in the care organization that would contribute to the care of the patient. While some existing systems may be adequate for broadcasting notice to all members of a defined group, or centralizing use of a single EHR, they do not resolve the problem of patients such as those with multiple physical, psychological, and/or social care needs, who rely upon one or more third party payors, and where, for example, there may be statutory, regulatory, and/or ethical needs to limit notice of care decisions to subsets of the provider group due to concerns of confidentiality or privacy. Nor do current systems provide a method by which a patient's care team can be effectively identified and managed on the basis of the nature and frequency of actual interaction with the individual. In addition, existing systems do not allow for timely and automatic flagging and distribution of immediate notice to diverse care providers providing inconsistent or medically conflicting directives to an individual that may be harmful or even life threatening. Existing systems do not avoid the problem of redundancy experienced by providers who must reenter data in electronic records maintained in the database of their own practices so as to participate in a care plan management system operating in a different database language. Other problems with current care plan systems include the inability to automatically filter sensitive data from a data stream without manual intervention, review, and redaction. There currently exists no comprehensive system that allows real-time extraction of sensitive patient information from comprehensive EHR plans during the transmission process.

SUMMARY OF THE INVENTION

The invention herein disclosed involves preparing, modifying and administering a coordinated health care plan for a patient receiving services from multiple providers, such as within an ACO structure, with a principal goal of improving communication among those providers and their patient while selectively limiting distribution of information on a need-to-know or similar basis, as may be constrained by regulatory, ethical, or patient-decision limitations. The invention provides a method and system for maintaining a centralized, unitary care plan that can be updated by multiple providers communicating in a plurality of machine or database languages with immediate notification to other select providers, payors, and the patient themself in each party's respective database language as needed. The invention involves the use of a centralized software solution ("Care Plan Manager" or "CPM) running on a plan manager "server" (actual or virtual) receiving input in various machine languages from multiple sources and transforming those languages into unitary "data objects" for storage and processing. Other related stored data objects are identified and retrieved to create full context data objects, which are systematically evaluated against applicable criteria for further action, including notification of specified parties relating to the newly created data objects. The newly created data object packages can then be transformed into one or more machine languages associated with other need-to-know/allowed-to-know parties and transmitted to those parties. The method disclosed herein further provides the ability to automatically filter sensitive data from a data stream in the transmission process without manual intervention, review, and redaction. At any given time, the patient has the ability to view their current care plan embodied as relevant stored data objects by initiating a data object inquiry and care plan construction and transmission. Unlike other care plan management systems that require the user to rewrite care plan and related medical information into the care plan system in order to fully participate, the current invention avoids the need for double entry of data. The invention allows automatic cross-updating of a health care plan from different providers for an individual: if one doctor changes/adds to the plan, other providers can be selectively alerted with the opportunity to comment/agree/disagree. One or more participating parties may be provided with the option of over-ruling changes made by one or more other providers.

The invention may be viewed as having five key characteristics:

Aggregation of a care plan (centralization) for a patient
Creation of an assigned care team for the patient under the plan
Provision of an appropriate, secure communications system among the care team and patient using a plurality of database languages regarding the plan
Distribution of the care plan and notice of clinical events selectively among providers, payors, the patient, and other authorized parties
Management of tasks (task management/prioritization of tasks) for the patient as the patient navigates their care plan.

DETAILED DESCRIPTION

In the following paragraphs, the present invention is described in detail by way of example with reference to the attached drawings. The examples shown should be considered as exemplars, rather than as limitations, of the present invention. As used in this specification, "present invention" refers to any one of the embodiments described herein and any equivalents. Furthermore, reference to a feature or various features of the present invention does not mean that all claimed embodiments or methods must include the referenced feature or features. Throughout this description there is reference to the "system." The system herein referred to can include any collection of communicating databases, processors, communication devices, transmitters, receivers, and networks.

Figure 1:
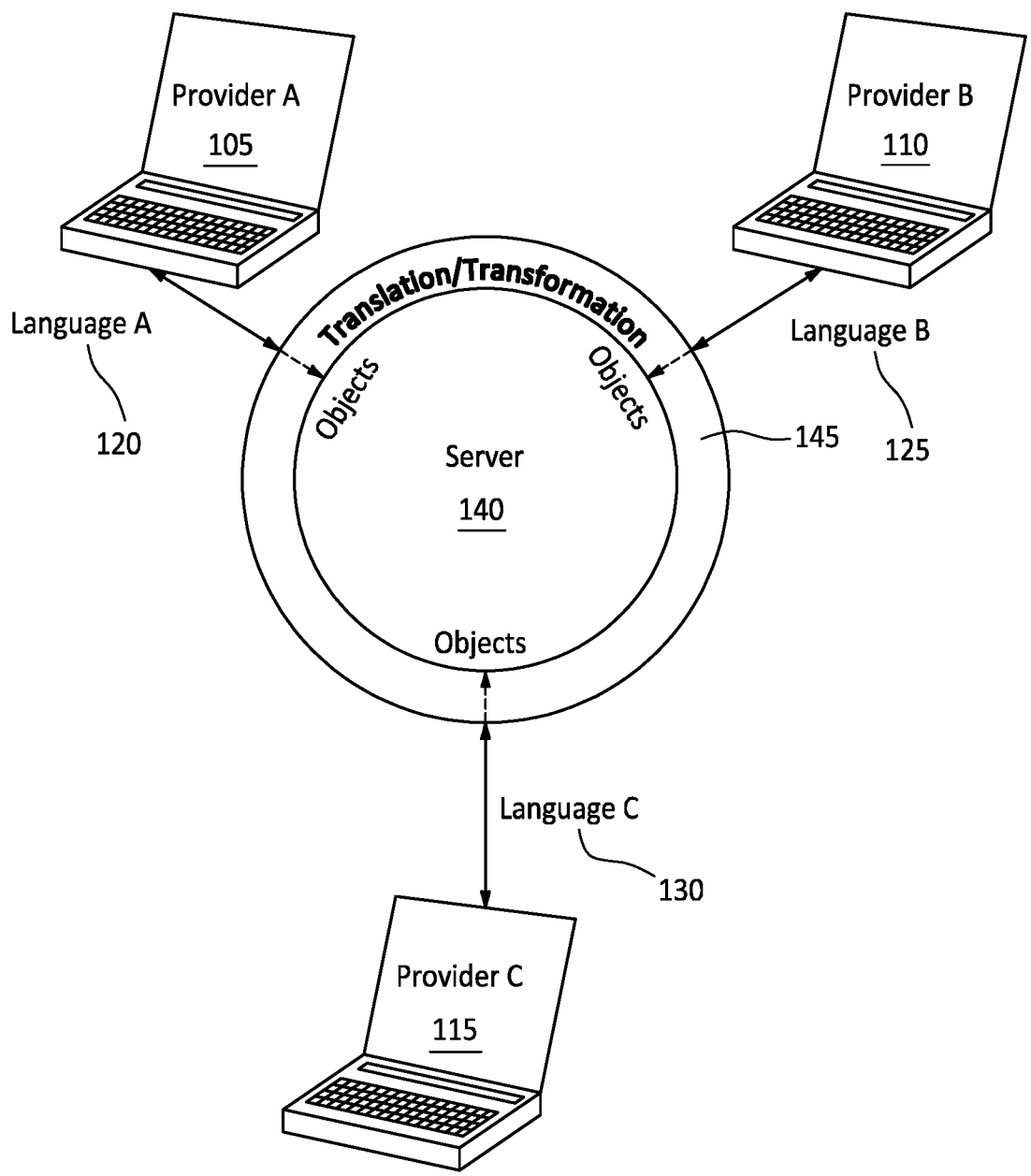
FIG. 1 provides a simplified overview of a process for a plurality of provider nodes communicating in different machine languages with a centralized server.

The present invention relies upon coordinated communications from external nodes 105, 110, 115 associated with a person as depicted in simplified fashion in FIG. 1. Each node consists of at least a data transmitter and data receiver, and incorporates or is associated with a central processing unit (CPU), memory, a display, an input device, and a network interface. Examples of such nodes include, but are not limited to, laptops, desktops, tablets, and mobile devices. The nodes may be connected to the internet directly or through an internal network. There may be any number of nodes, each of which is communicating directly or indirectly with a centralized server 140 through a network, and each using a database language 120, 125, 130 that may be different from each other and from the languages used by other nodes. The nodes may or may not be capable of communicating directly with each other. The nodes must be capable of creating, viewing, and/or storing data, and each is capable of transmitting and receiving data through the network. Each node may represent a user with a medical or health maintenance relationship to the patient that may be described within one or more categories of care such as insurance services, social services, shelters, primary care, hospital care, in-home care, adult day care, rehabilitative therapy, emergency or urgent care, nursing home care, health clubs, facilities for debilitating brain diseases, hospice or palliative care, specialist medical care, or care or assistance for mental health, addiction rehabilitation, assisted living, brain disorders, or nutrition. A node may be the patient themself.

Data regarding a patient may be maintained or transmitted by a node in an EHR by categories (e.g., prescribed drugs, diagnosis, condition, treatment type) that are identified by codes. Different providers may use different coding sets (e.g., LOINC, RXNorm, SNOWMED), and sometimes combinations thereof (e.g., LOINC and SNOWMED).

In addition to differing coding systems, there are multiple database languages that providers may employ to communicate EHR's and request or otherwise exchange information over the internet. For example, Health Level Seven (HL7) is a currently common set of clinical standards and messaging formats that provides one framework for the management, integration, exchange, and retrieval of electronic information across different healthcare systems. Many health systems and many providers, however, have not implemented it. HL7 does not dictate system architecture or how data is stored in an application. Additional prevalent machine languages include without limitation ANSI, DIRECT, SOAP, REST, and Delimited File.

Whatever may be a node's machine or database language and coding system, information is often transmitted from the node in a form that may be described as data objects. Generally, a data object is a collection of one or more data points that, collectively, may standalone and provide meaning as a whole. Examples of data objects are data tables, arrays, pointers, records, files, sets, and scalar types. Data objects may vary across database structures and different machine and database languages.

The current invention concerns communication and processing of data objects or other form of input information by a "centralized server." The "centralized" aspect of the "centralized server" 140 does not imply that the server is located in a single location. Rather, the "centralized server" may be one or any number of devices consisting of one or more processors (collectively, "CPM Processor"), including storage units, that execute a variety of software and that function as a unified unit to receive, process, store, and transmit data. Coded information may be communicated with a CPM Processor 140 using each node's respective database language 120, 125, 130 (e.g., HL7). Each node may be preauthorized to receive data from, and to transmit data to, the centralized server. The process may include encryption prior to transmission.

Figure 2:
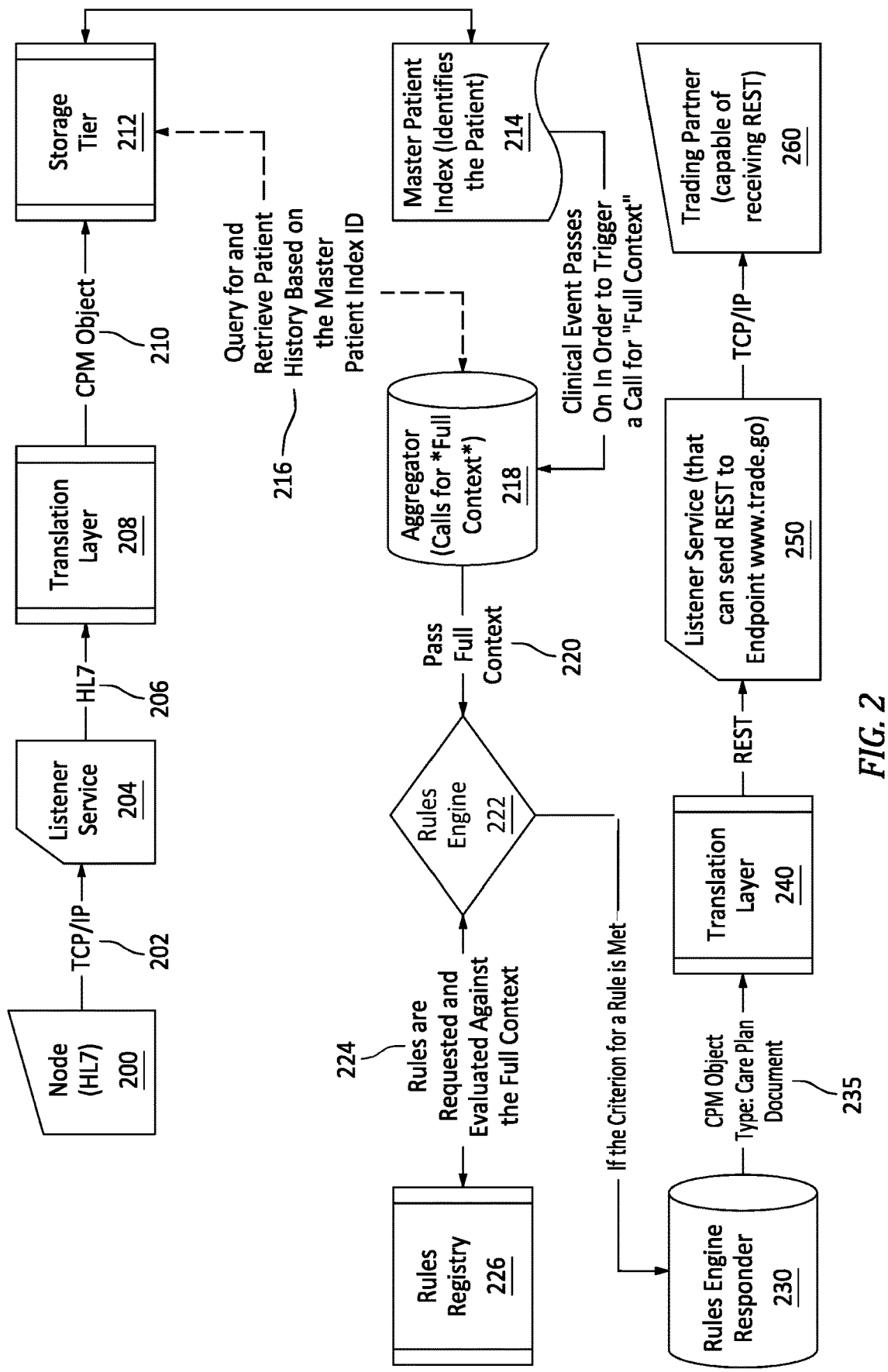
FIG. 2 illustrates an exemplary flow of information and decision making through a CPM centralized server.

A more detailed depiction of a preferred embodiment of the current invention is provided in FIG. 2. As there shown, and as described in detail below, the embodiment may be understood as a layered, centralized software solution hosted on one or multiple servers comprising: a listener service 204 receiving data in bits/bytes 202 from external user nodes 200; (ii) a translator 208 creating standardized objects 210; (ii) a storage tier 212; (ii) an aggregator 218 communicating 216 with the storage tier and with a (iv) a "rules engine" 222 associated with a Rules Registry 226; and (v) a rules engine responder or routing service 230. The same or separate listening service and translator may be employed to transmit 240, 250 data to the external nodes 260. The embodiment of the solution may also include a master patient index 214 in communication with the storage tier and aggregator.

As illustrated, whatever coding format and language are used by a node 200, which in the example is HL7, the data from the node will be converted into bits and bytes and transmitted and targeted, typically using TCP/IP protocols 202, to a port of a listener service 204 at the CPM Processor that is capable of accepting the information in the node's database language. The data may then be conveyed in the received language, e.g., HL7 206, from the listener service to the translator (or data transformer) 208.

Figure 3:
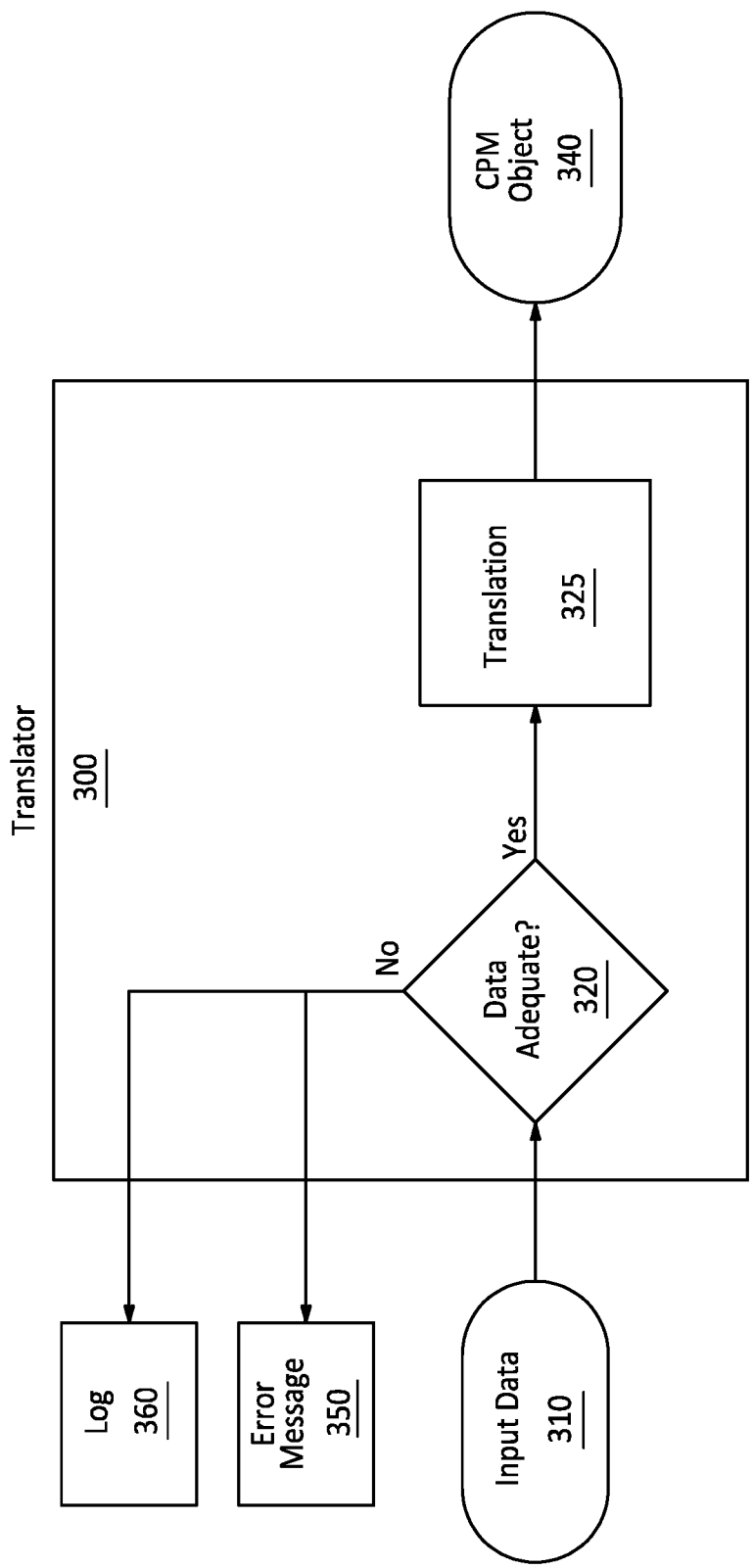
FIG. 3 illustrates flow of data through a translator to create a CPM Object.

The translator acts as a sort of "rosetta stone" for electronic messaging, appropriately translating data from each node for processing by the CPM Processor and translating CPM Objects, as discussed below, back to the various nodes' languages. The translator is able to parse a variety of message types and coding formats. As shown in FIG. 3, the translator 300 may scan each datum or data object 310 as it arrives to determine whether the data package is adequate to be transformed into a standardized CPM Object 320. For example, the incoming information may be required to have at least one key identifier. If the data are inadequate, the translator may generate an error message 350, which may be returned to the source node, and the event may be logged 360 for a period of time and possibly then deleted. If the data are adequate, the data are translated and any institutional coding formats from the node are translated 325 to the standardized coding format. Once the institutional codes are translated and the other parts of the messages are validated, the translator may then reconstruct each message as a standardized CPM Object 340 for transmission to storage.

The translator overcomes the problem of typical software packages that are commercially available for managing care plans within an institutional setting. To utilize such packages, it is necessary for data to be entered into the system in a database language that is compatible with the database language of the software package. Such packages do not allow input from a variety of otherwise unrelated entities using diverse database languages. Similarly, these software packages are typically unable to distribute data to users employing dissimilar database languages in a manner that allows integration of the data from the centralized source into the diverse users' EHR system without manual reentry of data into those systems using their specific database languages. The current invention overcomes that problem.

CPM Objects preferably have certain characteristics, including that they can be (1) stored, (2) aggregated, (3) reviewed to satisfy rules logic, (4) rearranged to convey relevant information, and (5) adapted to "longitudinal" care management programs that incorporate information from multiple care providers relating to disease prevention and treatment goals and plans over time. These CPM Objects may also have metadata properties or attributes such as patient ID, patient name, patient insurance, date of birth, telephone numbers, and others.

Figure 4:
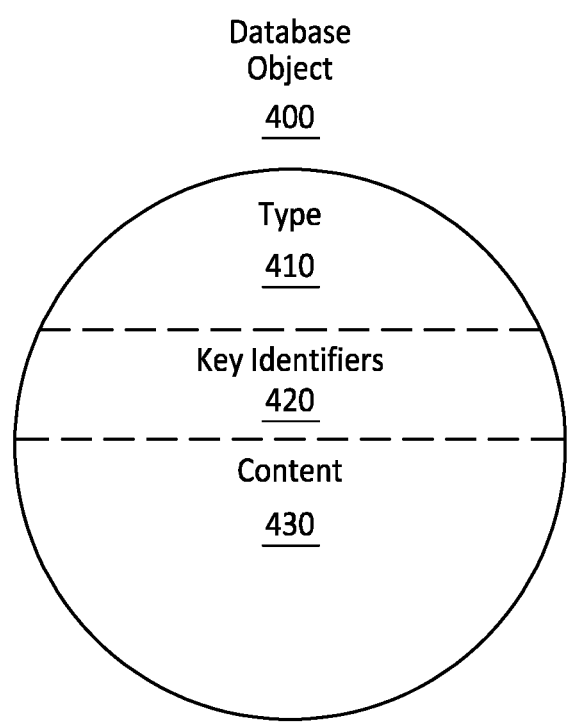
FIG. 4 shows a conceptual structure of a CPM Object.

A possible structure of a CPM Object 400 may be conceptualized as shown in FIG. 4. As there illustrated, such an object may have three characteristics. First is object type 410, which may provide a description of the data content by category. Each object may also include one or more key identifiers 420. A key identifier may be, for example, a unique identifier of the node from which the data originated and may be preserved throughout the process. Some identifiers may be created or assigned based upon the data received; for example, a unique alphanumeric character to unambiguously identify a particular local medical record number or an accession number. The key identifiers may also include system generated identifiers, such as master patient index identifiers or primary key identifiers. Finally, the data object includes the content 430, which is the substance of the information being conveyed.

An example of an object type is an "assignment object," which conveys information that the patient has been assigned to a specified facility. The metadata associated with this type of object may include the identity of the provider making the assignment and the date or dates on which the patient is to attend the facility. Another object type may be "care plan document object." This type of object is particularly significant because it may contain an entire care plan submitted by a provider. Other examples of CBM objects include, without limitation, payment authorization objects; laboratory results objects, and self-reported vitals objects.

In the embodiment shown in FIG. 2, the CPM Processor directs the CPM Object from the translator to a storage tier 212, where copies of most CPM Objects are maintained by the CPM Processor. Software operating within the CPM Processor then directs a number of inquiries.

A first inquiry may be made to a Master Patient Index (MPI) 214 to determine whether the CPM Object is associated with a patient of record. An MPI identifies individual patients by assigning a unique identifier to that person and may include demographic information relating to the person. This may be done by storing information such as name, date of birth, gender, etc., and assigning each patient a unique identifier regardless of what facility or other system participant originated the patient or is the patient's principle contact. In the context of this invention as applied to an ACO, an MPI identifies patients across separate clinical, financial, and administrative systems and helps to consolidate patients from all facilities participating in the ACO or similar system.

If the CPM Object is associated with a patient of record, the CPM Object may be incorporated into a new CPM Object to be retained in the storage tier associating the object with patient information contained in the MPI. The CPM Object may also be directed to a CPM aggregator step ("Aggregator") 218. The purpose of the Aggregator is to aggregate, into an aggregate data object ("Full Context Object") 220, data within the system that may be relevant to the event associated with the new CPM Object. The Aggregator creates aggregate objects by querying and retrieving other data objects 216 from the storage tier. A Full Context Object thus may contain other standardized data objects that originated from data provided by other external nodes. These may include data objects originating, for example, from a primary care physician containing the patient's medication, from a counselor concerning substance use, from a social worker concerning shelter, from an insurer concerning payment authorization, from a laboratory concerning blood testing results, and/or from the patient concerning self-reported vitals objects. Aggregation may be by reference, such that Full Context Objects may or may not have a part or may have different parts at different times, and different Full Context Objects may share the same part. The CPM Processor may then pass the Full Context Object embodying the new event and the collected data objects to the Rules Engine 222.

Figure 5:
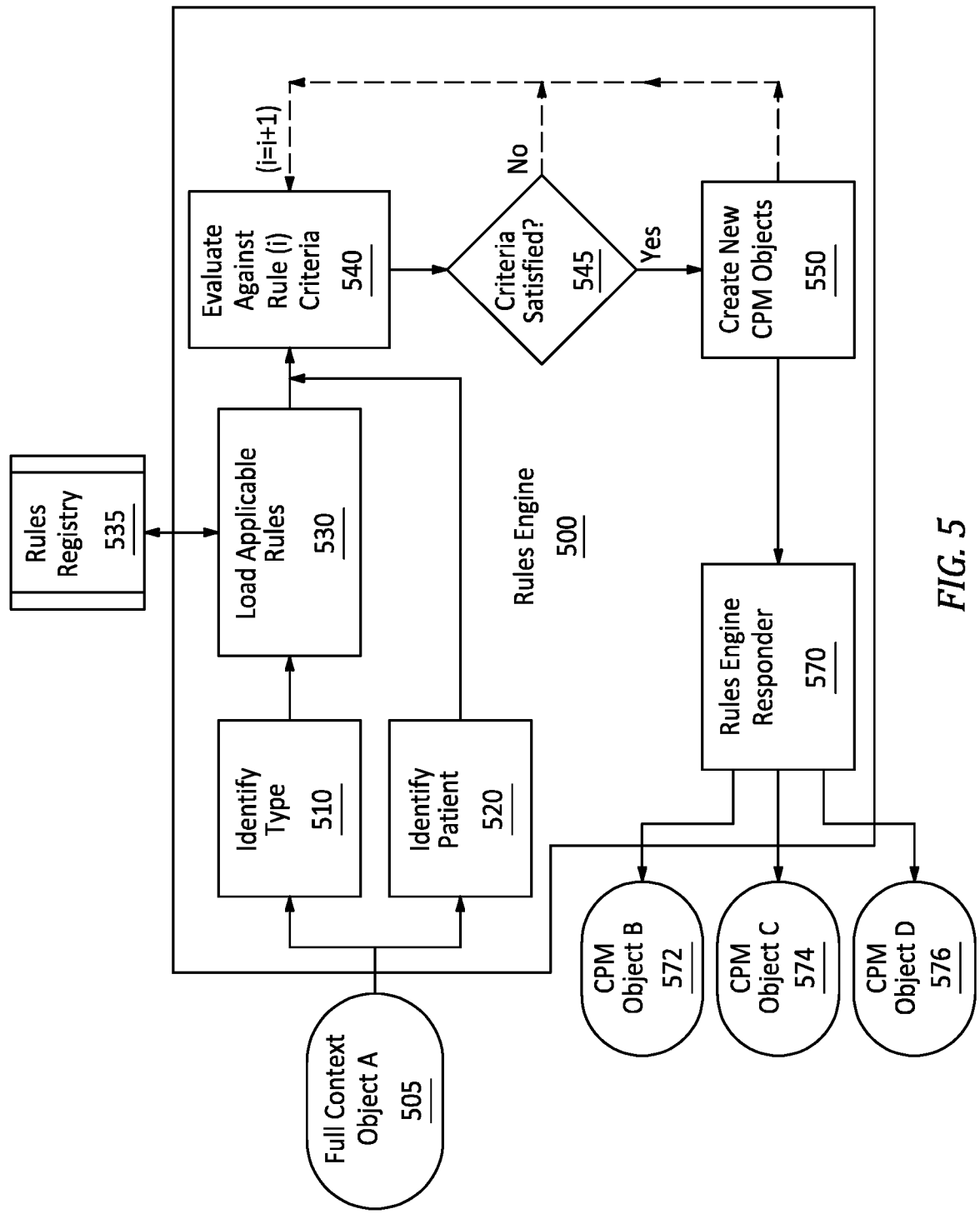
FIG. 5 shows steps involved in processing an object through a rules engine.

The Rules Engine 500 utilizes sets of instructions, or sets of modules or procedures, to evaluate the Full Context Objects 505 it receives. In the embodiment shown in FIG. 5, it does so by first identifying the object type 510 and the patient 520 as a key identifier associated with the object content of the Full Context Object 505. The Rules Engine may then load from a rules repository, or "Rules Registry," 535, applicable rules 530, which may be determined, for example, by the object type. The rules may have been created by any number of interested parties, such as system users, but typically will be activated and managed by authorized administrative users according to specified parameters. Each rule is, in substantial part, a set of criteria against which data in a Full Context Object is assessed.

The rules engine thus assesses the object against the criteria 540 from the Rules Registry, which may be done iteratively, and, if a particular criterion or set of criteria are satisfied, the rule is initiated and prescribed action or actions are undertaken. The actions may involve modifying or creating one or more post-rule evaluation CPM Objects 550 that incorporate the rule satisfaction event. The Rules Engine Responder 570, according to further criteria, may then select appropriate objects to transmit and determine the destination of the new objects. The process does not need to be in this particular order; for example, the new CPM Objects may be created as part of the Rules Engine Responder process.

Figure 6:
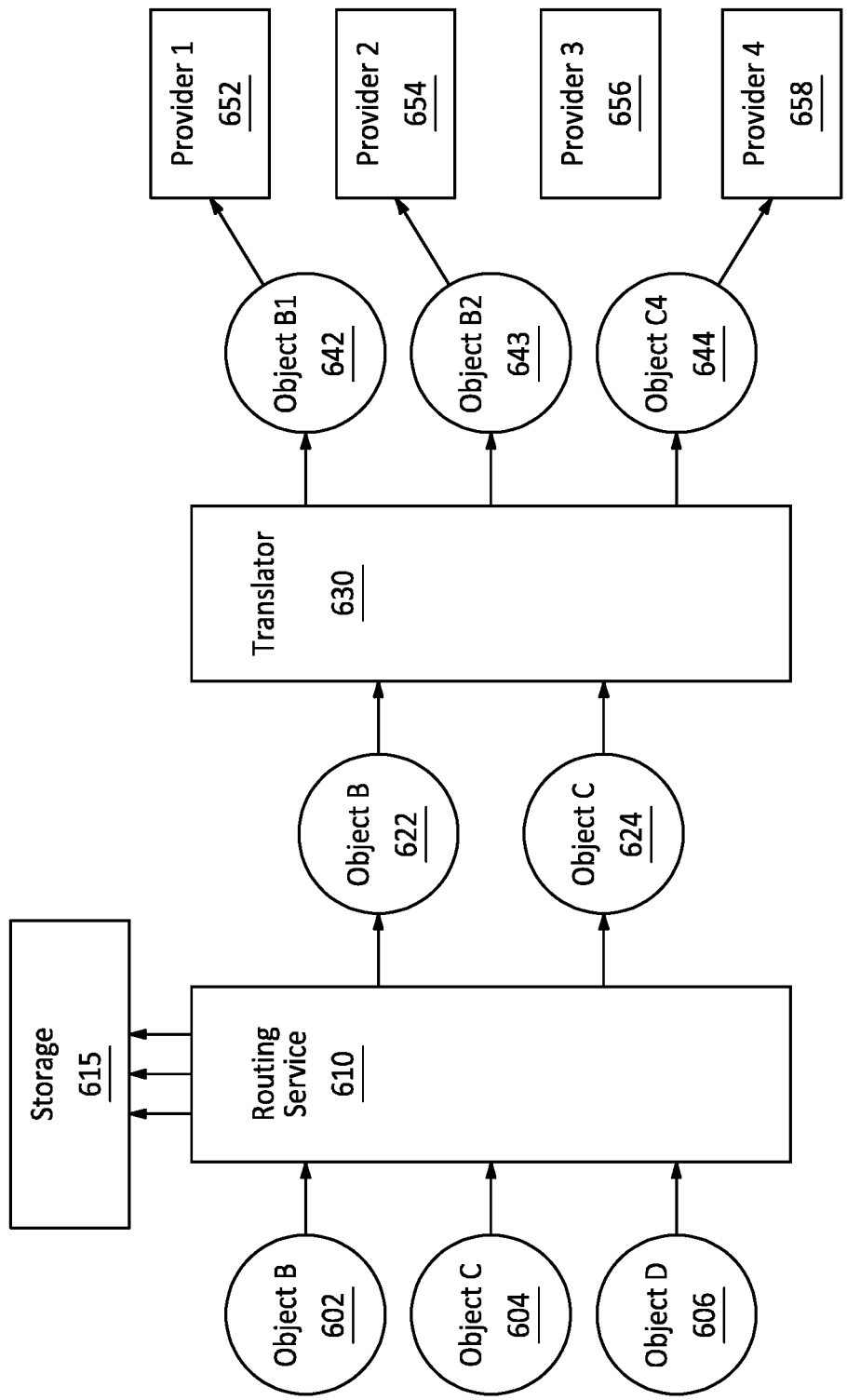
FIG. 6 illustrates a process for distributing new objects created by the rules engine.

Several new objects reflecting impacts of the new event may be created 602, 604, 606 in this manner, as now shown in FIG. 6. The rules engine responder, or routing service 610, selects the appropriate objects to transmit and their destination according to the satisfied rule or rules. The purpose of the routing service is to determine whether and where to direct new objects, which may include to storage 615 and to external nodes that application of the rules has determined have a need to know of the content of the object, or from which the system has determined that additional information is needed. Such a situation may occur, by way of further example, when the rules engine, pursuant to specified criteria, has determined that consent is required to send certain data to a specified provider node. Key identifiers, which may include, for example, medical record number, visit or encounter number, subscriber number for insurance plans, and accession number, may be maintained in routed objects.

Each new CPM Object with the data to be shared externally is then sent back through the translator 630, where the CPM Objects to be distributed externally 622, 624 are converted into objects 642, 643, 644 in the database language of the intended recipient or recipients. Those objects may then be transmitted to the intended recipients 652, 654, 658. In the example shown in FIG. 6, Object B 622 is translated into the machine language of Provider 1 to become Object B1 642, and also into the machine language of Provider 2 to become Object B2 643, before they are sent by way of, for example, the TCP/IP protocol, to Provider 1 652 and Provider 2 654, respectively. Object C is sent only to Provider 4 658, in that provider's machine language 644. Because the routing service has determined that no content needs to be sent to Provider 3 656, no object is sent to that provider.

Not all new objects will be sent to an external node. For example, as suggested in FIG. 6, the routing service may determine that Object D contains information that needs only to be stored and not further processed. The system may be set to have the routing service rout a copy of all new objects into storage 615.

By way of example, a Provider 1 node may submit clinical event data to the CPM indicating that the provider has authorized and assigned Individual K for substance abuse treatment at Facility X. Those data would be translated into a new CPM Object and incorporated into a full context object that includes the fact of the assignment by Provider 1. Upon receipt by the Rules Engine, a set of assignment rules may be invoked from the rules registry that include a criterion of pre-payment for specified care at Facility X. The Rules Engine would test the CPM Object as to whether it includes an authorization flag establishing receipt of payment by Facility X for the specified care. If the payment criterion is not satisfied, then no further object is created such that assignment to Facility X is not effected, or a new object may be created identifying non-payment for the specified care. Conversely, if the full context object contains data indicating that the payment criterion is satisfied then the rules engine responder may then be called upon to effect the assignment to Facility X, assuming satisfaction of other applicable criteria. This may involve creation of various objects to inform other nodes, such as the patient's insurer, Facility X, and possibly other providers of the assignment.

By way of further example, the assignment to a substance abuse facility may implicate information that is confidential or otherwise subject to restricted distribution due to patient preference. Data reflecting such restriction may be maintained in storage as a data "flag" as part of a data object associated with Individual K, which, upon receipt of a new event object relating to Individual K would be called by the Aggregator and incorporated into the Full Context Object when created. Subsequently, the object may be tested in the Rules Engine against a criterion of whether such a flag exists within the object. If satisfied, distribution of the Object or its successor in transmission may then be restricted in accordance with the specifics of that rule.

By way of another example, the clinical event submitted by Provider 1 may be the submission of a new care plan for Individual K. Translation may transform these data into a CPM care plan document object, which would be passed to the storage tier. The Aggregator would then incorporate into a Full Context Object other objects existing within storage relating to Individual K. The Rules Engine may process the Full Context Object against a rule from the Rule Registry applying criteria of whether another care plan exists for Individual K. If the object satisfies that criterion, the rules engine responder may be instructed to create a data object with information that informs each of the providers that has submitted a care plan for Individual K. The rules engine may further assess the new Full Context Object against a series of criteria from the rules registry requiring consistency between specified aspects of the plans and flagging substantive inconsistencies that are identified. Satisfaction of one of more of these criteria may further invoke the rules engine responder to initiate transmission of one or more additional objects to deliver information to each of the providers alerting them to the conflict.

The Rules Engine may consider whether there has been one or more other versions of a clinical event provided by another node. For example, the new clinical event may be a medication that Provider 1 has ordered for Individual K. The Aggregator may find that there is a pre-existing object within storage showing that Provider 2 has also prescribed certain medication for Individual K and will incorporate that data into a Full Context Object. The Rules Engine may then determine, based upon medication criteria populated in the Rules Registry, that the medication that Provider 1 had prescribed contraindicates the medication ordered by Provider 2. The rules engine responder may then create an object that contains these data for transmittal to both Providers 1 and 2. One or more objects may be created to signify a "high priority" or "danger" level notice for translation and transmission to both providers.

By way of further example, Provider 1 may submit data to the plan management system indicating that a CT scan for a patient is needed and is being ordered, which data will be converted into a standardized CPM Object. If an object is present within the storage tier system indicating a CT scan ordered for the patient by Provider 2, that object will be incorporated with the new CPM Object into a Full Context Object. Criteria from the rules registry when applied by the Rules Engine will lead to the creation of a new object to be translated and sent at least to Provider 1 informing the provider of the existence and availability of the CT scan for the patient.

The process and associated access is not limited to providers and payors. For example, an external node may be a patient portal, where the patient is authorized to access their CPM information. From the node, the patient may submit a "request object" in the machine language of their node for their "complete" care plan, which would be received on a port of the CPM listener service and then translated into a standardized CPM request data object. The request data object would go to CPM storage, which could communicate with the Master Patient Index to confirm that the CPM Object is associated with a patient of record. Upon confirmation, the CPM processor may direct the CPM Object to the CPM aggregator, from which a "full context" call is made back to the storage tier to retrieve care plan data maintained for the patient. The Aggregator may then aggregate all non-expired care plan objects that are in storage for the patient. These retrieved data are populated as a full context object in the Rules Engine and assessed against criteria determining relevancy of each datum to the patient's care plan. The rules engine responder then assembles the data satisfying the applicable criteria into the patient's collective plan, creating a comprehensive CPM data object that is the patient's CPM plan. The CPM object is then passed through the translation layer to transform the object into an object in the database language of the patient's receiving device and sent to that device. The patient could then view their complete plan on their device. Distribution of the comprehensive care plan object could be restricted by the rules within the Rules Registry as may be determined by the patient and their providers.

The CPM may also be used to identify and manage a patient's care team through specified criteria developed from appropriate standards and algorithms. Criteria within the Rules Registry may be established by which a provider may become a member of Individual K's care team if the provider passes specified qualitative and quantitative criteria. These criteria may involve type of provider role, qualifications, and number and types of clinical events initiated by the provider. For example, upon receipt of a new object signifying a clinical event for Individual K submitted by Provider 3, the resulting CPM Object, after incorporation into a full context CPM Object, may be assessed by the Rules Engine for, among other criteria, whether the event and Provider 1's medical role relative to Individual K qualify Provider 1 to be a member of the person's care team. For example, a simplified version of a rule may be that an object identifying a provider that passes the cardiologist criterion, a cardiological information criterion, and minimum number of interventions criterion will cause the creation of a new object that, in part, is an invitation/authorization to Provider 1 to become a member of the patient's care team. Additional rules in the Rules Registry may provide that all members of a patient's care team are to be provided notice of specified events. The patient, by accessing the care plan through the system, may at any time find out who their current care team comprises.

As a person well versed in the relevant trade would know, the system described herein is applicable to any number of nodes, whether providers, patients, or others. Similarly, there is no inherent limit on the number or types of data points or objects that may apply to any given patient.

Insofar as the description above and the accompanying drawings disclose any additional subject matter that is not within the scope of the claims below, the inventions are not dedicated to the public and the right to file one or more applications to claim such additional inventions is reserved. While the inventions claimed involve the steps stated below, the invention encompasses any rational ordering of the steps presented.

The invention claimed is:

1. A system comprising a centralized server:
   providing access for a plurality of authorized or authenticated external nodes to communicate in machine language with the centralized server, where each external node
      comprises at least a data transmitter and a data receiver in association with a processor, and
      is preauthorized or authenticated to transmit data to and receive data from the centralized server;
   receiving a first communication from a first external node expressed in a first machine language, where the first communication contains data relating to a person and the first machine language differs from the machine language of at least one other of the plurality of external nodes;
   passing the first communication from the first external node through a transformation process, whereby the first communication is transformed into at least a first standardized data object comprising a first collection of information including data contained in the first communication;
   storing the first standardized data object in a data storage tier associated with the centralized software solution and containing a plurality of other data objects;
   evaluating one or more of said plurality of other data objects to identify a first set of one or more other data objects that contain data relating to the person;
   aggregating, with the data of the first standardized data object, data from the first set of one or more other data objects to create a first full context data object, wherein the first full context data object contains the aggregated data;
   evaluating the first full context data object relative to at least one first criterion;
   identifying, in response to the evaluation, a second external node for receipt of data contained in the first full context data object and creating a second standardized data object with data from the first full context data object relating to the person for transmission to the second external node if the first full context data object satisfies the at least one first criterion;
   transforming the second standardized data object into a second communication, where the second communication:
      consists of a second data set, where the second data set comprises data from the second standardized data object relating to the person; and
      is expressed in the machine language of the second external node; and
   transmitting the second communication to the second external node.

2. The system of claim 1 wherein the first standardized object and the data therein can be stored, reviewed relative to criteria, modified, rearranged, and aggregated with other standardized objects.

3. The system of claim 1, further comprising the central server:
   accessing a master patient index database for a first set of identification data associated with the person and adding at least one datum from said first set of identification data to the full context object prior to evaluating the full context object relative to the at least one criterion.

4. The system of claim 3, wherein the master patient index database comprises aggregated data identifying a plurality of patients from a plurality of separate data systems communicating with the centralized software solution.

5. The system of claim 1, where the first communication further includes:
   a first data set, where the first data set further comprises at least one first key identifier.

6. The system of claim 1, where the first standardized data object comprises a collection of information specifying at least:
   a first data type;
   the first key identifier; and
   at least one datum of the first data set relating to the person.

7. The system of claim 6, wherein the first key identifier is one of a medical record number, visit number, encounter number, subscriber number, or accession number associated with the person.

8. The system of claim 6, wherein the first key identifier is also contained in the full context object and in the second standardized data object.

9. The system of claim 1 wherein each processor includes at least a central processing unit, memory, a display, an input device, and a network interface.

10. The system of claim 1 wherein the first standardized object comprises an object type identifier, a key identifier, and data content relating to medical or health maintenance care for the person.

11. The system of claim 10 wherein the first external node and the second external are providers of, or payors for, medical or social health maintenance care for the person and the medical or health maintenance care consists of at least one of insurance services, social services, shelters, primary care, hospital care, in-home care, adult day care, rehabilitative therapy, emergency or urgent care, nursing home care, health clubs, facilities for debilitating brain diseases, hospice or palliative care, specialist medical care, or care or assistance for mental health, addiction rehabilitation, assisted living, brain disorders, or nutrition.

12. The system of claim 1 wherein the passing the first communication from the first external node through a transformation process associated with the centralized software solution further includes evaluating the first communication, prior to transformation, for the presence of at least one key identifier and generating and returning to the first external node an error message if a key identifier is not found.

13. The system of claim 1, wherein aggregating is by reference.

14. The system of claim 1, wherein the second standardized data object also contains data expressing at least one result of the evaluation of full context data object relative to the at least one first criterion.

15. The system of claim 1, further comprising the centralized server:
   evaluating the second communication relative to at least a second criterion and redacting at least one datum from the second communication prior to transmitting the second communication if the second criterion is satisfied.

16. The system of claim 1, wherein the machine language of the second external node is different from the machine language of the first external node.

17. The system of claim 1, wherein the centralized server stores a copy of the second standardized object in the storage tier.

18. The system of claim 1, further comprising the centralized server, after transmitting the second communication to the second external node:
- receiving a third communication from the first external node containing additional data relating to the person and creating a third standardized object containing at least one datum from the third communication;
- evaluating one or more of said plurality of other data objects to identify a third set of one or more other data objects that contain data relating to the person;
- aggregating, with the third standardized data object, data from the third set of other data objects to create a second full context data object, wherein the second full context data object contains the third standardized data object and data from the third set of other data objects;
- evaluating the second full context data object relative to at least one third criterion;
- in response to the evaluation, if the second full context data object satisfies the at least one third criterion,
  - identifying the first external node for receipt of data contained in the second full context data object;
  - creating a fourth standardized data object with data, from the second full context data object and related to data in the first standardized data object, for transmission to the first external node; and
- modifying the first standardized object.

* * * * *